United States Patent
Zimmer et al.

(10) Patent No.: US 8,226,793 B2
(45) Date of Patent: Jul. 24, 2012

(54) PROCESS AND DEVICE FOR PRODUCING AN ANALYTICAL TAPE FOR LIQUID SAMPLES

(75) Inventors: Volker Zimmer, Dossenheim (DE); Joachim Hoenes, Zwingenberg (DE); Werner Ruhl, Limbergerhof (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1691 days.

(21) Appl. No.: 11/123,311

(22) Filed: May 6, 2005

(65) Prior Publication Data

US 2006/0002816 A1    Jan. 5, 2006

(30) Foreign Application Priority Data

May 7, 2004  (DE) .......................... 10 2004 024 041

(51) Int. Cl.
*B29C 65/00*  (2006.01)
(52) U.S. Cl. .......... 156/302; 156/289; 156/297; 422/56; 422/58; 436/170
(58) Field of Classification Search ............... 422/56, 422/58; 436/170; 156/289, 297, 302
See application file for complete search history.

(56) References Cited

U.S. PATENT DOCUMENTS

| | | | | |
|---|---|---|---|---|
| 3,408,276 A * | 10/1968 | Rey | ........................... | 204/157.63 |
| 4,218,421 A | 8/1980 | Mack, Jr. et al. | | |
| 4,328,057 A | 5/1982 | Gutow | | |
| 4,328,184 A * | 5/1982 | Kondo | ............................. | 422/58 |
| 4,452,887 A | 6/1984 | Kitajima et al. | | |
| 4,475,969 A * | 10/1984 | Reed | .............................. | 156/152 |
| 4,665,139 A * | 5/1987 | Veazey et al. | .................... | 526/86 |
| 4,878,971 A * | 11/1989 | Tsunekawa et al. | ........... | 156/70 |
| 4,922,775 A * | 5/1990 | Winter | ............................ | 83/333 |
| 5,077,010 A * | 12/1991 | Ishizaka et al. | ................. | 422/56 |
| 5,079,174 A * | 1/1992 | Buck et al. | ..................... | 436/538 |
| 5,096,836 A | 3/1992 | Macho et al. | | |
| 5,200,148 A | 4/1993 | Saito | | |
| 5,679,311 A * | 10/1997 | Harttig et al. | ................. | 422/102 |
| 5,725,717 A * | 3/1998 | Harte et al. | .................... | 156/299 |
| 6,036,919 A * | 3/2000 | Thym et al. | ..................... | 422/426 |
| 6,207,000 B1 * | 3/2001 | Schwobel et al. | ............. | 156/248 |
| 6,357,503 B1 | 3/2002 | Kromer et al. | | |
| 6,395,957 B1 * | 5/2002 | Chen et al. | .................... | 604/381 |

(Continued)

FOREIGN PATENT DOCUMENTS

DE          3714662          11/1988

(Continued)

OTHER PUBLICATIONS

English machine translation of DE19940279.*

*Primary Examiner* — Philip Tucker
*Assistant Examiner* — Nickolas Harm
(74) *Attorney, Agent, or Firm* — Bose McKinney & Evans LLP

(57) ABSTRACT

The invention concerns a process for producing an analytical tape for liquid samples in which a rollable transport tape is provided with test fields that are spaced apart in the direction of the tape for analyzing the liquid samples. A multilayered test label tape is prefabricated from at least a detection film and an adhesive tape and subsequently the test fields are transferred as self-adhesive test labels from the test label tape onto the transport tape.

14 Claims, 4 Drawing Sheets

U.S. PATENT DOCUMENTS

| | | | |
|---|---|---|---|
| 6,484,818 B2 * | 11/2002 | Alft et al. | 175/45 |
| 6,537,496 B1 * | 3/2003 | Knappe et al. | 422/58 |
| 2002/0015813 A1 * | 2/2002 | Pendry et al. | 428/41.8 |

FOREIGN PATENT DOCUMENTS

| | | |
|---|---|---|
| DE | 3727667 | 3/1989 |
| DE | 3729352 | 3/1989 |
| DE | 19836644 | 2/2000 |
| DE | 19940279 | 3/2001 |
| GB | 1073596 | 6/1967 |
| JP | 62-239104 | 10/1987 |
| WO | WO 02/100274 A1 | 12/2002 |

* cited by examiner

PROCESS AND DEVICE FOR PRODUCING AN ANALYTICAL TAPE FOR LIQUID SAMPLES

REFERENCE TO RELATED APPLICATIONS

The present application claims priority to German Patent Application No. 10 2004 024 041.8, filed May 7, 2004 which is hereby incorporated by reference in its entirety.

TECHNICAL FIELD

The invention concerns a process and a device for producing an analytical tape as well as the corresponding product.

BACKGROUND

Analytical tapes can be used for determining blood sugar in portable test instruments which can also be simply and rapidly used by laymen to carry out the required analytical steps. An example of analytical tape in the form of a tape cassette is described in U.S. Pat. No. 5,077,010.

SUMMARY

A process and device as well as a suitable analytical tape which enables an automated tape manufacture without complicated handling steps is provided. Instead of conventional individual test strips, a plurality of test fields with a suitable test chemistry are successively arranged on the analytical tape that is wound up in a spool-like manner. In operation of the resulting analytical tape, a body fluid is applied to a test field that is brought into an active position by advancing the tape in order to then enable a detection inside the instrument, a non-limiting example of which is by an optical measuring unit. This enables a large number of tests to be carried out without requiring a separate handling and disposal of disposable test strips.

The present invention simplifies layered tape construction by a two-step process. Accordingly, a test label tape is pre-manufactured comprising at least a detection film and an adhesive tape. The test fields are transferred from the test label tape onto a transport tape as self-adhesive test labels. The labelling process allows a simple positioning and attachment of the test fields as the transport tape passes through. This allows a continuous processing in a production line without requiring a kinematically complex handling by pick-and-place devices.

According to the present invention a process for producing an analytical tape for liquid samples is provided. The process comprises the steps of: providing a rollable transport tape providing a test label tape including at least a detection film and an adhesive tape and transferring test fields as self-adhesive test labels from the test label tape onto the transport tape wherein the test fields are spaced apart in the direction of the transport tape for analysing the liquid samples.

In addition, according to the present invention a device for producing an analytical tape for liquid samples is provided. The devices comprises a conveying device operating from roll-to-roll for a rollable transport tape, and a labelling device for labelling test labels including at least a detection film and an adhesive tape onto the passing transport tape at a labelling site.

Still further, according to the present invention an analytical tape for liquid samples is provided. The analytical tape comprises a rollable transport tape and test fields for analysing liquid samples applied to the transport tape, the test fields being self-adhesive test labels including at least a detection film and an adhesive tape and are labelled onto the transport tape.

These and other features of the present invention will be more fully understood from the following detailed description of the invention taken together with the accompanying claims. It is noted that the scope of the claims is defined by the recitations therein and not by the specific discussion of the features set forth in the present description.

BRIEF DESCRIPTION OF THE DRAWINGS

The invention is elucidated in more detail in the following on the basis of the examples shown schematically in the drawing.

Figure 1:
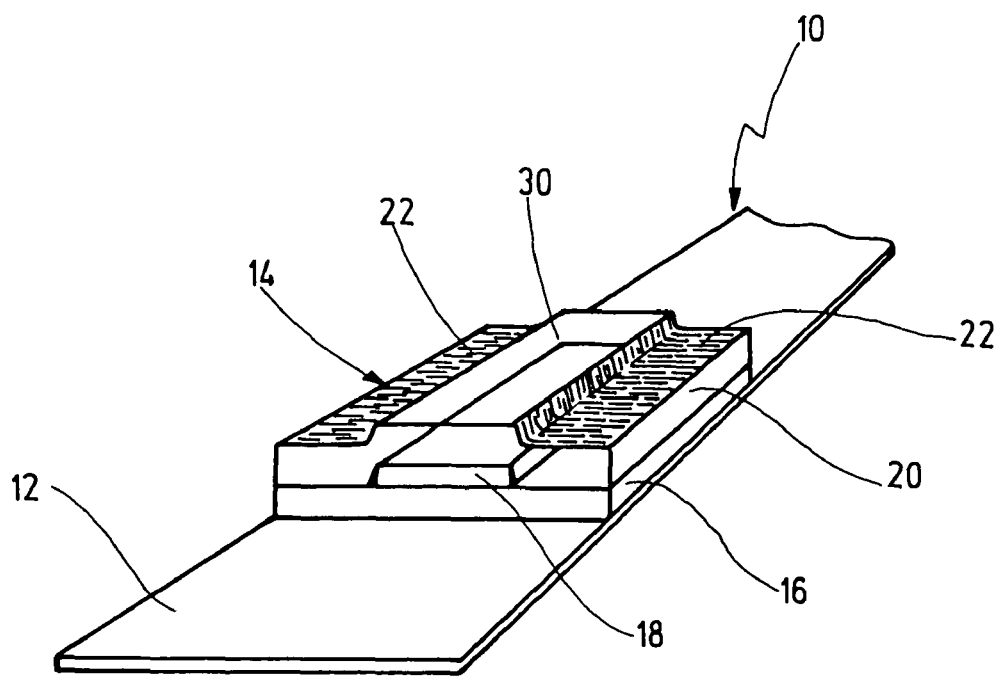
FIG. 1 shows an analytical tape with a multilayered test field in a sectional perspective view.

Skilled artisans appreciate that elements in the figures are illustrated for simplicity and clarity and have not necessarily been drawn to scale.

In order that the invention may be more readily understood, reference is made to the following examples, which are intended to illustrate the invention, but not limit the scope thereof.

DETAILED DESCRIPTION OF THE DRAWINGS

The analytical tapes 10 shown in the drawings comprise a rollable transport tape 12 with a plurality of test fields 14 that are applied thereto and spaced apart in the direction of the tape for analysing body fluids and in particular blood.

As shown in FIG. 1 the test fields 14 are multilayered and in the form of self-adhesive test labels. They each comprise a section of an adhesive tape 16, a detection film 18 and an absorbent cover layer 20 some areas of which are furnished with an impregnation 22.

Figure 2:
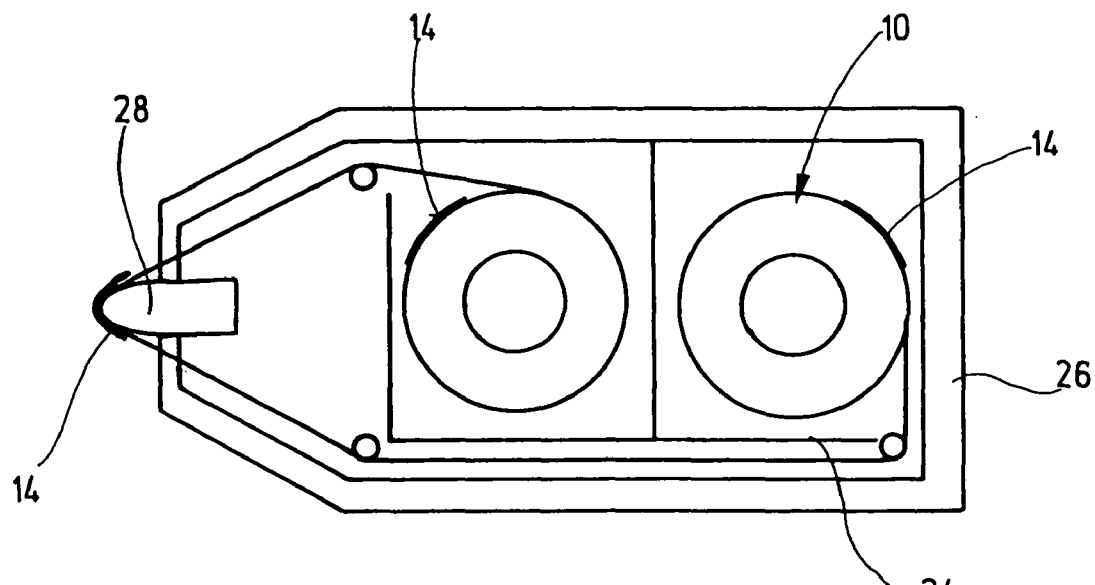
FIG. 2 shows a test instrument with the analytical tape used therein in cross-section.

According to FIG. 2 the reel of analytical tape 10 is used in the form of a cassette 24 in a portable blood sugar test instrument 26. Winding the tape forwards exposes the individual test fields or test labels 14 in the area of a measuring head 28 in order to apply a drop of blood for the glucose determination. The liquid is taken up in a central detection zone 30 of the cover layer 20 where the impregnated edge strips 22 limit the spread of liquid. Due to their multilayered structure, the test fields 14 have a certain height while the thin flexible transport tape 12 in the intermediate areas allows a reliable sealing against sealing elements thus enabling a reliable storage which is protected against the effects of the environment.

The analytical tape 10 is produced by a roll-to-roll processing in two process steps. In the first step according to FIGS. 3 to 8, a test label tape 32 is firstly prefabricated whereupon the self-adhesive test labels 14 are transferred from the test label tape 32 onto the transport tape 12 in the second step according to FIG. 9.

The test fields 14 are adhesively attached by bonding one adhesive side of a double-sided adhesive tape to the detection film and the other adhesive side (in the form of self-adhesive labels) to the transport tape 12.

In order to increase the reliability of the process, the adhesive tape may be stabilized by an intermediate foil that is coated on both sides with adhesive.

Additionally, the detection film is applied to the adhesive tape while keeping lateral strips of tape free. In order to achieve a uniform sample distribution the detection film can be covered by a cover layer which is in the form of a fabric or fleece where the cover layer is wider than the detection film and is held by the adhesive tape in the area of its overhanging edges.

Figure 3A:
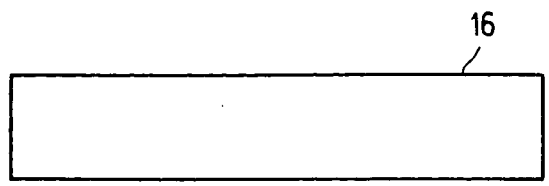
FIGS. 3 to 6 show various constructional stages of a test label tape forming the test fields in each case in a top-view and in cross-section.
Figure 3B:
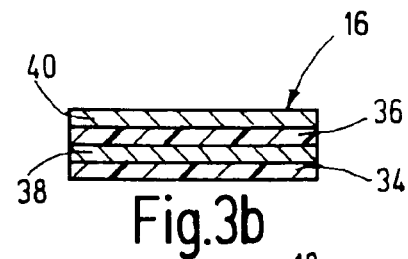
Figure 4A:
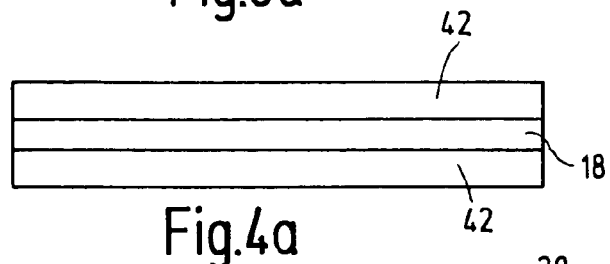
Figure 4B:
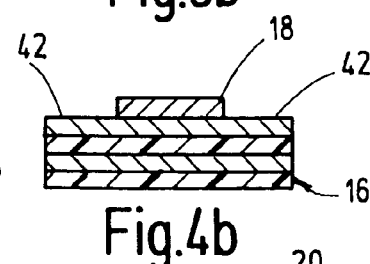
Figure 5A:
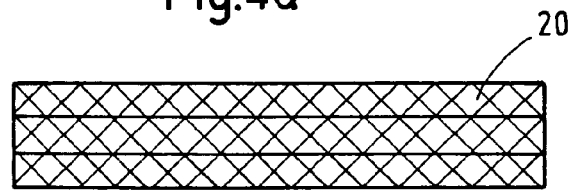
Figure 5B:
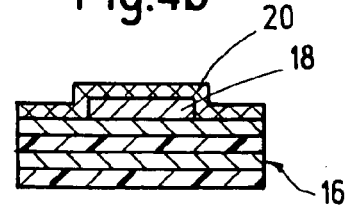
Figure 6A:
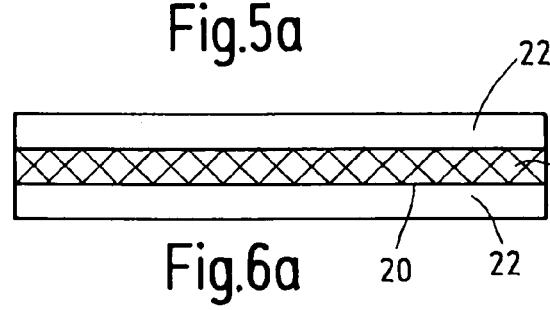
Figure 6B:
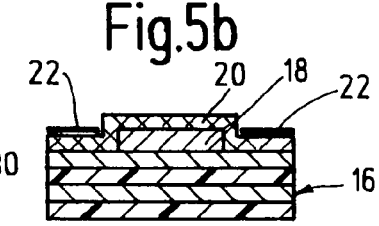

As illustrated in the top-view of FIG. 3a and in the cross-section of FIG. 3b—which are not shown to scale—the double-sided adhesive tape 16 forms the base of the test label tape 32. This has a carrier sheet 34 or a release liner for tape transport from a feed spool to a take-up spool through various processing stations. On the carrier sheet 34 there are two adhesive layers 38, 40 which are separated by an intermediate layer 36. According to FIG. 4 a detection film 18 of narrow width is glued centrally onto the upper free adhesive layer 40 of the adhesive tape 16 as it passes through such that lateral strips of adhesive 42 of the adhesive layer 40 are kept free. Afterwards the cover layer 20 in the form of a fabric is applied as a tape according to FIG. 5. The cover layer 20 is wider than the detection film 18 and is therefore attached by the free adhesive strips 42 in the area of its laterally protruding edges. The protruding edge strips of the cover layer 20 outside the detection film 18 are subsequently printed with a water-repellent impregnation 22 such that only the central detection zone 30 can absorb the body fluid that is applied whose spread is then limited (FIG. 6). In addition water-repellent impregnation outside the detection zone may further reduce required amount of sample.

The process may be simplified by printing on the impregnation as a strip at the side of the detection film by a printing process. It is also conceivable that the fibres of a filament structure forming the cover layer are already coated with an impregnation agent.

With regard to the production process, the adhesive tape can be processed by a carrier sheet from roll-to-roll. In this case the test labels can be produced as detachable generally flat structures on a carrier sheet of the adhesive tape by cutting or punching.

The feed during passage can be achieved by detaching the test labels from the carrier sheet of the adhesive tape by deflection over a dispensing edge and labelling them onto the transport tape as it is transported from roll-to-roll.

Figure 7:
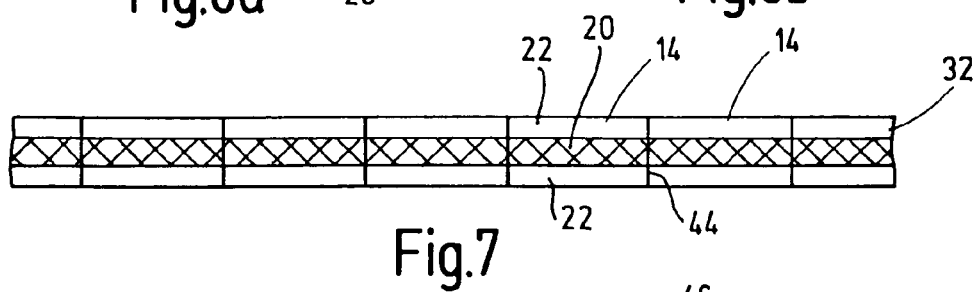
FIG. 7 shows the test label tape cut into individual test labels in a sectional top-view.
Figure 8:
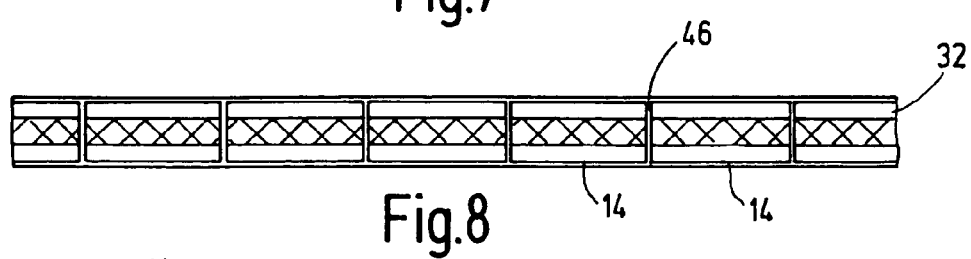
FIG. 8 shows a punched test label tape in a view corresponding to FIG. 7.

Individual test labels 14 can be cut out of a test label tape 32 manufactured in this manner as detachable generally flat structures according to FIG. 7. As such, the labelling device comprises a punching or cutting device located before the labelling site for dividing the adhesive tape furnished with the detection film into self-adhesive test labels. For this purpose cuts 44 that run perpendicular to the direction of the tape are introduced for example by laser cutting from the cover layer 20 down to the depth of the carrier sheet 34 such that the test labels 14 with the adhesive layer 38 can be detached. Instead of the cutting process they can also be separated by punching according to FIG. 8 in which case the punching grid 46 is removed from the label tape 32 to expose the labels 14.

Figure 9:
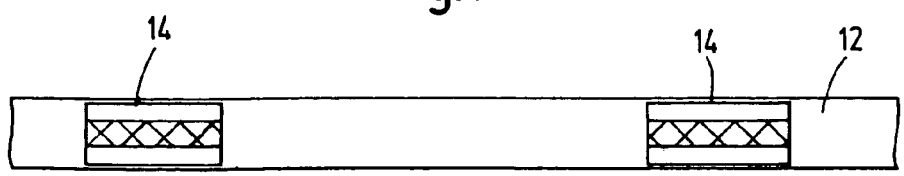
FIG. 9 shows a top-view of the analytical tape of FIG. 1.

In the second step of the process the transport tape 12 is guided from a feed roll to a take-up roll during which the individual labels 14 are applied spaced apart at a labelling station according FIG. 9. For this purpose the test labels 14 are detached from the carrier sheet 34 of the adhesive tape 16 by deflection over a dispensing edge and pressed onto the transport tape 12 in a self-adhesive manner by means of the exposed adhesive layer 38.

The process principle described above can also be used for an economic production in a multitrack process. For an economical concurrent processing, a multitrack test label tape can be formed by several detection films next to one another on an adhesive tape. This allows the multitrack test label tape to be divided in sections into multiple test labels by cutting or punching. Alternatively it is also possible that sections of the multitrack test label tape are divided by cutting or punching into label blocks comprising several individual test labels next to one another. The multiple test labels or the label blocks can then be labelled onto the transport tape spaced apart from one another and subsequently the transport tape is divided longitudinally into individual tracks.

With regard to the device, a conveying device operating from roll-to-roll for a rollable transport tape and a labelling device for labelling a test label comprising at least a detection film and an adhesive tape onto a labelling position on the transport tape as it passes is provided.

Figure 10:
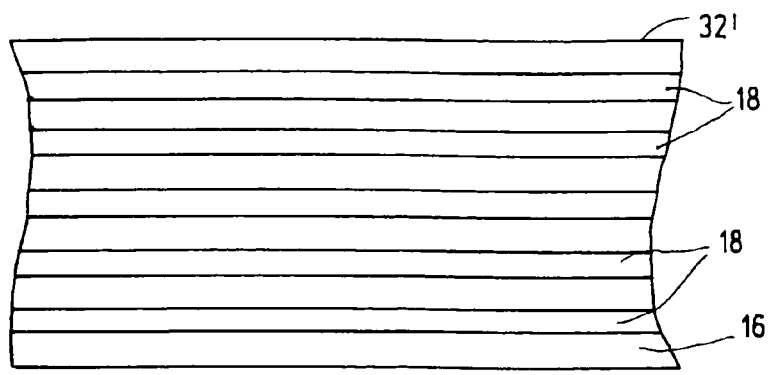
FIGS. 10 to 13 show various steps of a multitrack manufacture of analytical tapes in a sectional top-view.
Figure 11:
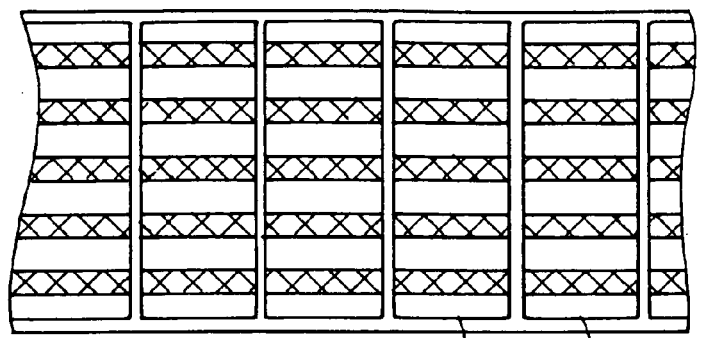
Figure 12:
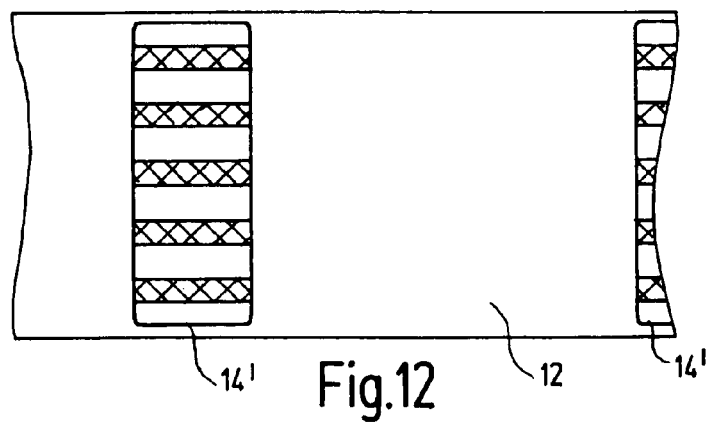
Figure 13:
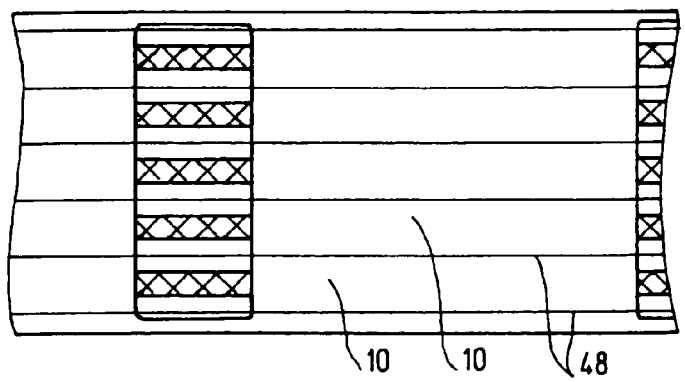
Figure 14:
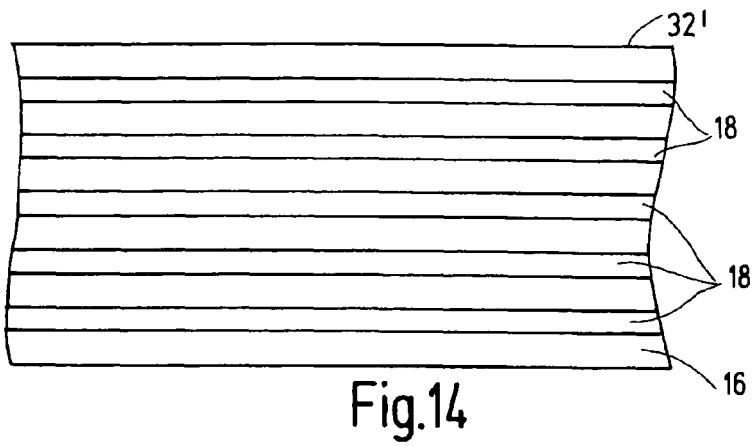
FIGS. 14 to 17 show another example of a multitrack manufacture in a view corresponding to FIG. 10 to 13.

For this purpose a multitrack test label tape 32' is formed according to FIG. 10 in the arrangement described above with several parallel detection tracks 18 on a wide adhesive tape 16. According to FIG. 11 this multitrack label tape 32' is divided in sections into multiple test labels 14' by punching and removing the punching grid. They can be labelled onto a wide transport tape 12 spaced apart from one another according to FIG. 12 whereupon the transport tape according to FIG. 13 is divided into individual tracks or individual analytical tapes 10 by longitudinal cuts 48.

Figure 15:
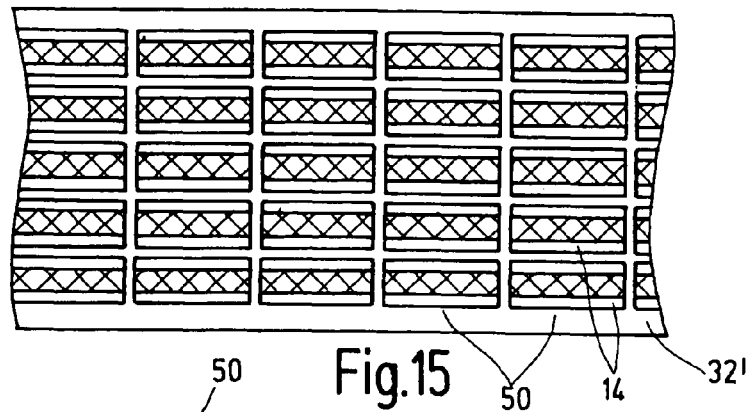
Figure 16:
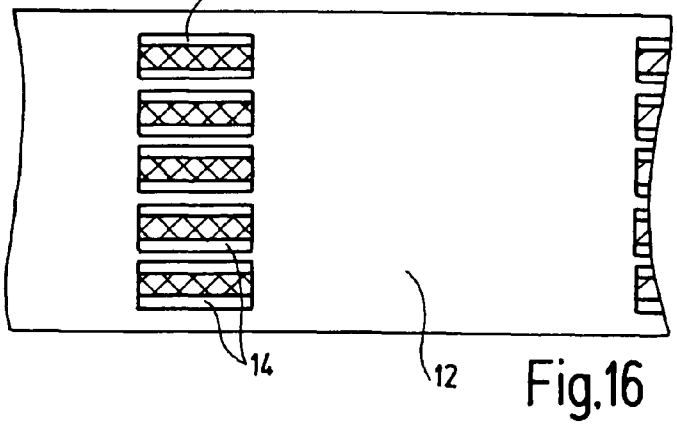
Figure 17:
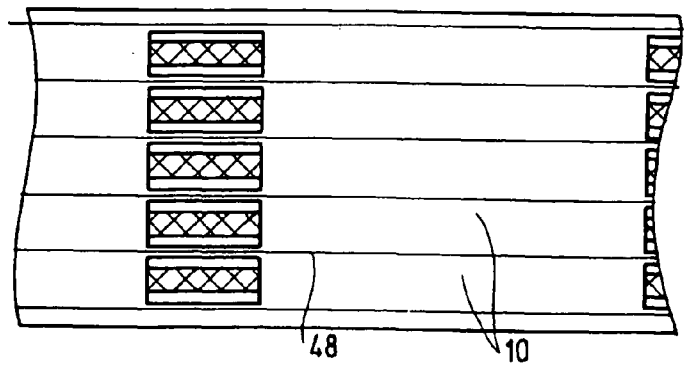

The example illustrated in FIGS. 14 to 17 differs essentially only in that instead of the multiple test labels 14', label blocks 50 consisting of several (in the present non-limiting example five) individual test labels 14' are formed in sections on the carrier tape 32' by punching (FIG. 15). These can then be labelled in blocks onto the transport tape 12 according to FIG. 16 in order to in turn obtain the individual analytical tapes 10 by longitudinal cuts 48.

An analytical tape 10 for liquid samples, a non-limiting example of which includes body fluids, comprises a rollable transport tape 12 and a plurality of test fields 14 mounted thereon for analysing liquid samples. The test fields 14 are prefabricated as self-adhesive test labels including at least a detection film and an adhesive tape and are labelled onto the transport tape.

Having described the invention in detail and by reference to specific embodiments thereof, it will be apparent that modification and variations are possible without departing from the scope of the invention defined in the appended claims. More specifically, although some aspects of the present invention are identified herein, it is contemplated that the present invention is not necessarily limed to these one aspects of the invention.

What is claimed is:
1. A process for producing an analytical tape for liquid samples, the process comprising the steps of:
   providing a rollable transport tape,
   forming a test label tape including at least a detection film and a double-sided adhesive tape, the forming of the test label tape comprising:

bonding the detection film to a first side of the adhesive tape while keeping lateral adhesive strips on the first side of the adhesive tape free, and cutting or punching the test label tape to form individual, detachable self-adhesive test labels, a second side of the double-sided adhesive tape forming a bottom adhesive side of the test labels, and transferring the self-adhesive test labels from the test label tape onto the transport tape, wherein the test labels are spaced apart in the direction of the transport tape and form test fields for analyzing the liquid samples, and wherein the bottom adhesive sides of the test labels are bonded to the transport tape.

2. The process of claim 1 wherein the adhesive tape is stabilized by an intermediate foil, which is coated on both sides with adhesive.

3. The process of claim 1 wherein the detection film is covered by a cover layer that is in the form of a fabric or fleece.

4. The process of claim 3 wherein the cover layer is wider than the detection film and is held by the adhesive tape.

5. The process of claim 3 wherein the cover layer is provided with a water-repellent impregnation outside a detection zone.

6. The process of claim 3 wherein an impregnation agent is printed in a strip shape at sides of the detection film by a printing process.

7. The process of claim 3 wherein a filament structure forming the cover layer is coated with an impregnation agent.

8. The process of claim 1 wherein the adhesive tape includes a carrier sheet, and the carrier sheet is transferred from a feed spool to a take-up spool.

9. The process of claim 1 wherein the test labels are produced as detachable generally flat structures on a carrier sheet of the adhesive tape by cutting or punching from a cover layer covering the detection film down to the depth of the carrier sheet.

10. The process of claim 1 wherein the adhesive tape includes a carrier sheet, the test labels are detached from the carrier sheet of the adhesive tape by deflection over a dispensing edge and labeled onto the transport tape, and the transport tape is transferred from a feed spool to a take-up spool.

11. The process of claim 1 wherein a multitrack test label tape is formed by several detection films next to one another on an adhesive tape.

12. The process of claim 11 wherein the multitrack test label tape is divided in sections into multiple test labels by cutting or punching.

13. The process of claim 12 wherein the multiple test labels or the label blocks are labeled spaced apart onto the transport tape and subsequently the transport tape is divided longitudinally into individual tracks.

14. The process of claim 11 wherein the multitrack test label tape is divided in sections into label blocks comprising several individual test labels lying next to one another by cutting or punching.

* * * * *